| United States Patent [19] | [11] 4,005,214 |
| Furlenmeier et al. | [45] Jan. 25, 1977 |

[54] WATER-SOLUBLE AMOXICILLIN SALTS

[75] Inventors: André Furlenmeier, Basel; Peter Quitt, Fullinsdorf, both of Switzerland

[73] Assignee: Hoffmann-La Roche Inc., Nutley, N.J.

[22] Filed: Aug. 11, 1975

[21] Appl. No.: 603,406

[30] Foreign Application Priority Data

Aug. 21, 1974 Switzerland ............... 11433/74
June 26, 1975 Switzerland ............... 8309/75

[52] U.S. Cl. .................. 424/271; 260/239.1
[51] Int. Cl.² ........................ C07D 499/68
[58] Field of Search ........... 260/239.1; 424/271

[56] References Cited

UNITED STATES PATENTS 3,674,776   7/1972   Long ............... 260/239.1

OTHER PUBLICATIONS

Chem. Abstr., vol. 76, 121441(x) (1972).

Primary Examiner—Gerald A. Schwartz
Attorney, Agent, or Firm—Samuel L. Welt; Bernard S. Leon; Gerald S. Rosen

[57] ABSTRACT

Choline and N-methyl-D-glucamine salts of amoxicillin, processes for their preparation and pharmaceutical compositions containing the salts as the active antibacterial component are disclosed.

4 Claims, No Drawings

WATER-SOLUBLE AMOXICILLIN SALTS

BACKGROUND OF THE INVENTION

Amoxicillin, D-(−)-alpha-amino-parahydroxybenzyl penicillin, is a semi-synthetic penicillin produced in accordance with the processes disclosed in U.S. Pat. No. 3,674,776. Certain of its salts are also known, i.e., hydrochloric, phosphoric, sulfuric, thiocyanic and beta-naphthalene sulfonic acid salts, and sodium and potassium salts.

The compound is readily formulated into stable oral dosage forms and is useful to treat bacterial infections. Amoxicillin is practically insoluble in water and aqueous solutions and therefore cannot be incorporated satisfactorily into parenteral formulations. In addition, the known salts of amoxicillin are unsuitable for use in parenteral formulations because, inter alia, they are unstable in aqueous media or cause irritation at the site of injection.

In order to form satisfactory injectable solutions of closely related semisynthetic penicillins, e.g., ampicillin, the usual method is to dissolve the sodium salt of the compound in the sterile water for injection and administer within an hour. For administration by intravenous drip, the sodium salt is isotonic sodium chloride, 5% dextrose in 0.4% aqueous sodium chloride solution, 10% invert sugar in water or a sodium lactate solution and administered as a very dilute, e.g., 0.2%, solution of ampicillin.

These known methods of producing injectable solutions are not suitable for amoxicillin since the sodium salt of amoxicillin is prepared at a pH of about 9 and amoxicillin is very unstable at such high pH's. In fact, amoxicillin is most stable at pH 7 but is relatively insoluble at that pH.

There is thus a need for a suitable form of amoxicillin which is amenable to inclusion in parenteral formulations and which performs satisfactorily when injected into the patient and retains the antibacterial activity of amoxicillin.

DESCRIPTION OF THE INVENTION

It has been discovered that the novel choline and N-methyl-D glucamine salts of amoxicillin not only form suitable parenteral solutions and meet the above criteria but also are suitable for use in oral and topical pharmaceutical preparations.

Both the choline and the N-methyl-D-glucamine salts of amoxicillin have antibacterial activity of the scope of the activity of amoxicillin. They possess a wide spectrum of activity against gram-positive and gram-negative microoganisms.

The salts provided by the present invention can be used for the treatment and prophylaxis of infectious diseases and as disinfection agents. Suitable dosages to combat bacterial infections vary with the patient being treated. However, individual dosages of about 0.25 g. to about 2 g. from one to four times per day can be administered to adults to achieve satisfactory results.

Because the salts provided by the present invention have excellent water-solubility (more than 10%), they are particularly suitable for parenteral administration.

The acute toxicity (LD 50 in mg./kg.) of the choline salt and of the N-methyl-D-glucamine salt of amoxicillin (compounds X and Y, respectively, in the table below) upon intravenous and subcutaneous administration to mice, as well as the activity (CD 50 in mg./kg.) of these two salts aginast Escherichia coli upon subcutaneous administration to mice are given in the following table.

| Compound | LD 50 mg./kg. i.v. | (Lethal Dose) s.c. | CD 50 mg./kg. (Curative Dose) |
|---|---|---|---|
| X | 250–500 | 2000–4000 | 5.9 |
| Y | 500–1000 | > 5000 | 5.0 |

Pharmaceutical preparations containing the choline salt or the N-methyl-D-glucamine salt of amoxicillin can be made with a compatible non-toxic pharmaceutical carrier material. Such a carrier material can be an organic or inorganic non-toxic inert carrier material suitable for enteral or in the preferred embodiment, parenteral administration, such as, for example, water, gelatin, gum arabic, lactose, starch, magnesium stearate and the like. The pharmaceutical preparations can be made up in a solid form, e.g., as tablets, dragees, suppositories or capsules or, preferably, in a liquid form, e.g., as aqueous solutions. The pharmaceutical preparations may be sterilized and/or may contain adjuvants, salts for varying the osmotic pressure or buffers. The pharmaceutical preparations may also contain compatible therapeutically valuable materials other than the salts provided by the present invention. Preferably, the choline salt or the N-methyl-D-glucamine salt of amoxicillin is provided as a powder in a dry ampule. The vehicle most suitable for intramuscular (IM) and intravenous (IV) injection in conjunction with the active salts of this invention is sterile water. The concentration of salt in the IM and IV solutions is preferably sufficient to provide from about 5% to 25% by weight amoxicillin free acid based on the weight finished formulation. For use in intavenous drip administration, normal saline or a 5% aqueous dextrose solution are suitable. In the intravenous drip formulations the most suitable concentration of the active ingredient is that amount of the choline or N-methyl-D-glucamine salt which provides from about 0.2 to 5% by weight of amoxicillin free acid based on the weight of the finished formulation.

The choline salt and the N-methyl-D-glucamine salt of amoxicillin are manufactured by reacting amoxicillin or a hydrated form thereof with choline or N-methyl-D-glucamine, cleaving off any amino protecting group which may be present and isolating the thus obtained choline salt or N-methyl-D-glucamine salt of amoxicillin.

The amoxicillin used as the starting material can contain an amino group provided with a protecting group instead of a free amino group. Such a protected amino group is then converted, following the reaction with choline or N-methyl-D-glucamine, into a free amino group by conventional means. Thus, for example, an optionally substituted benzyloxycarbonylamino group can be re-converted into a free amino group by catalytic hydrogenation.

In the reaction of amoxicillin or a hydrated form thereof with choline or N-methyl-D-glucamine there are preferably used molar equivalent amounts of both reactants. However, a molar excess of up to about 10% of choline or N-methyl-D-glucamine can be used, if desired.

The reaction of amoxicillin or a hydrated form thereof with choline can be carried out in the presence of organic solvents, e.g., methanol, ethanol, dimethyl sulfoxide, dimethylformamide and the like, or a mixture thereof, or in the presence of water. The preferred solvent is ethanol.

The reaction of amoxicillin or a hydrated form thereof with N-methyl-D-glucamine can be carried out in the presence of organic solvents, e.g., methanol, dimethyl sulfoxide, dimethylformamide and the like, or a mixture thereof, or in the presence of water, or in the presence of a mixture of propyleneglycol with ethanol, propanol or isopropanol. The preferred solvents are methanol or a mixture of propyleneglycol with ethanol, propanol or isopropanol.

The reactions are conveniently carried out at a temperature between about 0° C. and 40° C.

When the reaction of amoxicillin or a hydrated form thereof with choline or N-methyl-D-glucamine is carried out in the presence of water as a solvent, the isolation of the choline salt or the N-methyl-D-glucamine salt of amoxicillin from the reaction mixture can be carried out by lyophilization.

When the reaction of amoxicillin or a hydrated form thereof with choline is carried out in the presence of methanol, ethanol, dimethyl sulfoxide, dimethyl-formamide or the like or a mixture thereof or when the reaction of amoxicillin or a hydrated form thereof with N-methyl-D-glucamine is carried out in the presence of methanol, dimethyl sulfoxide, dimethylformamide or the like or a mixture thereof, the isolation of the choline salt or the N-methyl-D-glucamine salt of amoxicillin from the reaction mixture can be carried out by stirring the reaction mixture in a second solvent in which the choline salt or the N-methyl-D-glucamine salt of amoxicillin is insoluble, e.g., diethylether, ethyl acetate or the like. At least 5 volumes of the second solvent are conveniently used per volume of the first solvent.

When the reaction N-methyl-D-glucamine with amoxicillin or a hydrated form thereof is carried out in a mixture of propyleneglycol with ethanol, propanol or isopropanol, there are conveniently used 30–50 volumes, preferably 40 volumes, of propyleneglycol per 100 volumes of ethanol and 60–100 volumes, preferably 75 volumes, of propyleneglycol per 100 volumes of propanol or isopropanol. When such a mixture of propyleneglycol with ethanol, propanol or isopropanol is used as a solvent, the N-methyl-D-glucamine salt of amoxicillin can be isolated from the reaction mixture by stirring the reaction mixture in a solvent in which the N-methyl-D-glucamine salt of amoxicillin is insoluble conveniently ethyl acetate, propanol or isopropanol. In order to precipitate the N-methyl-D-glucamine salt of amoxicillin, there are conveniently used 7 volumes of one of these three solvents per volume of the mixture of propyleneglycol with ethanol, propanol or isopropanol.

The following Examples illustrate the present invention:

EXAMPLE 1

Choline is added portionwise to a suspension of 4.2 g. of amoxicillin trihydrate in 150 ml. of water and stirred at 5° C. until almost complete dissolution has taken place. Undissolved material is filtered off under suction and the resulting filtrate is lyophilized. There is thus obtained the choline salt of amoxicillin. Melting point: about 130° C. $[\alpha]_D^{25} = +174.8°$ ($c = 1.0$ in water).

EXAMPLE 2

3 G. of N-methyl-D-glucamine are added to a suspension of 6 g. of amoxicillin trihydrate in 80 ml. of water and stirred at 5° C. Insoluble material is fitered off under suction and the resulting filtrate is lyophilized. There is thus obtained the N-methyl-D-glucamine salt of amoxicillin. Melting point: about 160° C. (decomposition). $[\alpha]_D^{25} = +133°$ ($c = 1$ in water).

EXAMPLE 3

An ethanolic solution of choline obtained by reacting 3.4 g. of choline chloride with 0.5 g. of sodium in 40 ml. of absolute ethanol and having the resulting precipitated sodium chloride filtered off is stirred at room temperature and treated with 8.4 g. of amoxicillin trihydrate. The resulting mixture is then stirred at room temperature for a further 5 minutes. Resulting insoluble material is filtered off under suction and the filtrate is introduced into 400 ml. of diethyl ether while stirring. There is thus obtained a compound which is identical with the product obtained in Example 1, i.e., the choline salt of amoxicillin.

EXAMPLE 4

A solution of 2.6 g. of choline in 50 ml. of absolute ethanol was reacted with 8.4 g. of amoxicillin with stirring. The resulting mixture is then stirred at room temperature for a further 5 minutes. Resulting insoluble material is filtered off under suction and the filtrate is introduced into 600 ml. of diethyl ether while stirring. The resulting precipitate is filtered off under suction, washed with diethyl ether and dried in vacuo at 40° C. There is thus obtained a compound which is identical to the product obtained in Example 1, i.e., the choline salt of amoxicillin.

EXAMPLE 5

8 G. of amoxicillin trihydrate are added to a stirred suspension of 4.3 g. of N-methyl-D-glucamine in 40 ml. of methanol. The resulting mixture is then stirred at room temperature for 5 minutes and resulting insoluble material is filtered off under suction. The resulting filtrate is then introduced into 400 ml. of ethyl acetate while stirring. The resulting precipitate is washed with ethyl acetate, filtered off under suction and dried at 40° C. There is thus obtained a compound which is identical with the product obtained in Example 2, i.e., N-methyl-D-glucamine salt of amoxicillin.

EXAMPLE 6

8 G. of amoxicillin trihydrate are added within 15 minutes to a suspension of 4.3 g. of N-methyl-D-glucamine in a mixture of 36 ml. of absolute ethanol and 14 ml. of propyleneglycol while being vigorously stirred at 5° C. The resulting mixture is then stirred at 5° C. for a further 60 minutes. The resulting precipitate is filtered off under suction and washed with a mixture of 7.2 ml. of ethanol and 2.8 ml. of propyleneglycol. The resulting filtrate is introduced into 300 ml. of isopropanol at −5° C. while stirring. The resulting precipitate is washed with isopropanol and diethyl ether and dried in vacuo at 40° C. There is thus obtained a compound which is identical with the product obtained in Example 2, i.e., N-methyl-D-glucamine salt of amoxicillin.

EXAMPLE 7

A lyophilizate of the following composition, based on 4 ml. of ready-for-use injection solution, is manufactured in a conventional manner:

| Ingredient | Amount |
| --- | --- |
| Choline salt of amoxicillin | 320 mg. |
| Methyl p-hydroxybenzoate | 1.1 mg. |
| Propyl p-hydroxybenzoate | 0.135 mg. |

EXAMPLE 8

A lyophilizate of the following composition, based on 4 ml. of ready-for-use injection solution, is manufactured in a conventional manner:

| Ingredient | Amount |
| --- | --- |
| N-methyl-D-glucamine salt of amoxicillin | 385 mg. |
| Methyl p-hydroxybenzoate | 1.1 mg. |
| Propyl p-hydroxybenzoate | 0.135 mg. |

EXAMPLE 9

640 Mg. of the choline salt of amoxicillin are filled into a dry ampule by conventional means. In order to prepare a ready-for-use injection solution, 5 ml. of sterile water or 5 ml. of a sterile physiological sodium chloride solution are added to the salt.

EXAMPLE 10

770 Mg. of the N-methyl-D-glucamine salt of amoxicillin are filled into a dry ampule by conventional means. In order to prepare a ready-for-use injection solution, 5 ml. of sterile water or 5 ml. of a sterile physiological sodium chloride solution are added to the salt.

We claim:
1. The choline salt of amoxicillin.
2. A parenteral solution suitable for intramuscular or intravenous administration containing as the active ingredient a sufficient amount of the choline salt of amoxicillin to provide a weight concentration of about 5% to 25% amoxicillin free acid.
3. An intravenous drip solution containing as the active ingredient a sufficient amount of the choline salt of amoxicillin to provide a weight concentration of about 0.2% 5% amoxicillin free acid.
4. An antibacterial pharmaceutical composition comprising an antibacterial amount of the choline salt of amoxicillin and a pharmaceutically acceptable carrier.

* * * * *